(12) United States Patent
Pollock et al.

(10) Patent No.: US 7,740,653 B1
(45) Date of Patent: *Jun. 22, 2010

(54) SINGLE-PIECE ENDOPROSTHESIS WITH HIGH EXPANSION RATIOS AND ATRAUMATIC ENDS

(75) Inventors: David T. Pollock, San Carlos, CA (US); Richard Newhauser, San Franciso, CA (US); Octavian Iancea, Fremont, CA (US)

(73) Assignee: Abbott Vascular Solutioms Inc., Santa Clara, CA (US)

( * ) Notice: Subject to any disclaimer, the term of this patent is extended or adjusted under 35 U.S.C. 154(b) by 1463 days.

This patent is subject to a terminal disclaimer.

(21) Appl. No.: 11/110,999

(22) Filed: Apr. 20, 2005

Related U.S. Application Data

(60) Division of application No. 10/090,473, filed on Mar. 4, 2002, now Pat. No. 6,942,690, which is a continuation-in-part of application No. 09/837,353, filed on Apr. 17, 2001, now abandoned, which is a continuation-in-part of application No. 09/546,966, filed on Apr. 11, 2000.

(51) Int. Cl.
*A61F 2/06* (2006.01)
*A61M 29/00* (2006.01)
(52) U.S. Cl. .................. 623/1.15; 623/1.13; 606/191; 606/195; 606/198; 606/109
(58) Field of Classification Search ............... 623/1.15, 623/1.25, 1.13; 606/108, 191, 198
See application file for complete search history.

(56) References Cited

U.S. PATENT DOCUMENTS

| | | | |
|---|---|---|---|
| 4,739,762 A | 4/1988 | Palmaz | |
| 4,776,337 A | 10/1988 | Palmaz | |
| 4,893,623 A * | 1/1990 | Rosenbluth | 606/192 |
| 5,035,706 A | 7/1991 | Gianturco et al. | |
| 5,102,417 A | 4/1992 | Palmaz | |
| 5,397,355 A | 3/1995 | Marin et al. | |
| 5,423,885 A | 6/1995 | Williams | |
| 5,591,197 A | 1/1997 | Orth et al. | |
| 5,593,417 A | 1/1997 | Rhodes | |
| 5,681,346 A | 10/1997 | Orth et al. | |
| 5,733,325 A | 3/1998 | Robinson et al. | |
| 5,746,766 A * | 5/1998 | Edoga | 623/1.2 |
| 5,759,192 A | 6/1998 | Saunders | |
| 5,769,882 A | 6/1998 | Fogarty et al. | |
| 5,780,807 A | 7/1998 | Saunders | |
| 5,800,526 A | 9/1998 | Anderson et al. | |
| 5,824,036 A | 10/1998 | Lauterjung | |
| 6,355,057 B1 * | 3/2002 | DeMarais et al. | 623/1.15 |

* cited by examiner

*Primary Examiner*—Vy Q Bui
(74) *Attorney, Agent, or Firm*—Fulwider Patton LLP

(57) ABSTRACT

A new endoluminal prosthesis for use in sealing a vascular graft to corporeal lumen provides for a flattened bulbous tail at the end of each cell of the prosthesis. The flattened bulbous tails reduce the amount of wear between the prosthesis and the softer material of the vascular grafts or corporeal lumen walls. A method of manufacturing a stent from a flat sheet of material is also included.

7 Claims, 13 Drawing Sheets

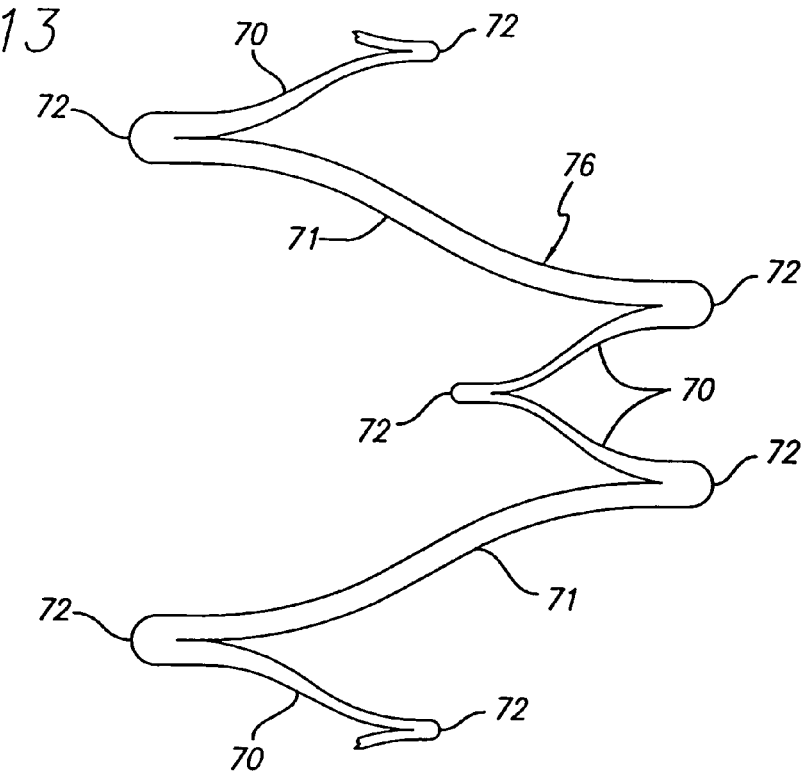
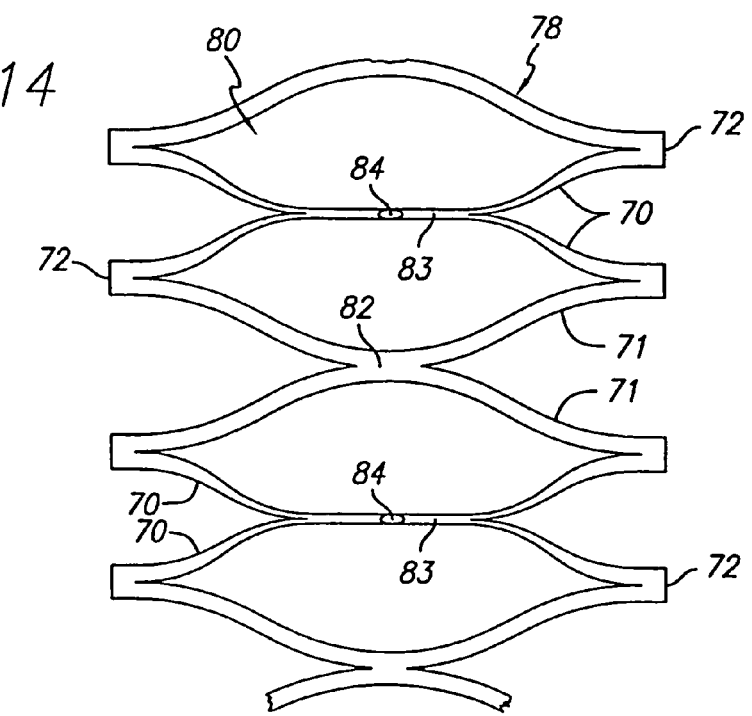

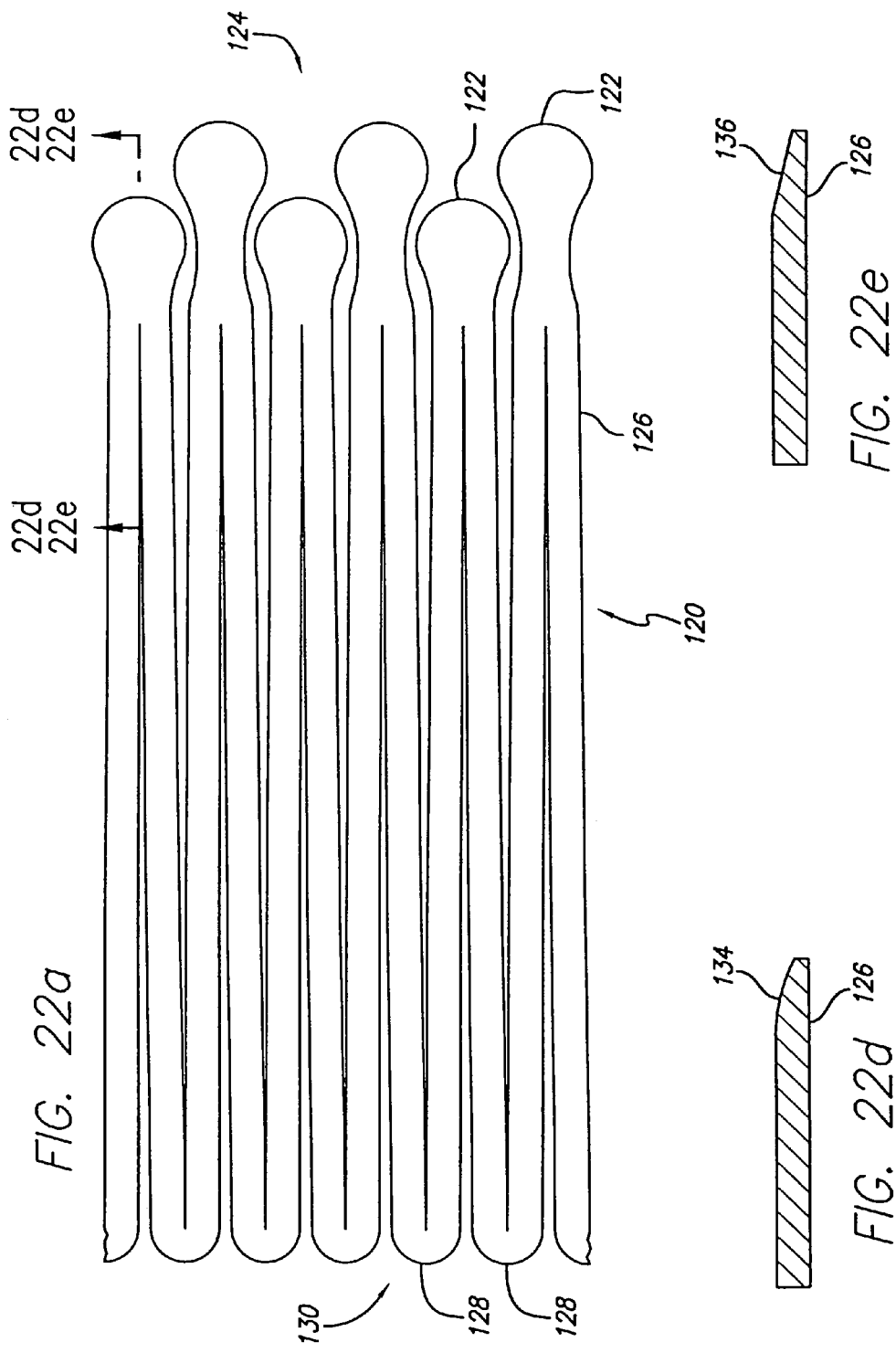

SINGLE-PIECE ENDOPROSTHESIS WITH HIGH EXPANSION RATIOS AND ATRAUMATIC ENDS

RELATED APPLICATIONS

This Application is a divisional of application Ser. No. 10/090,473 filed Mar. 4, 2002 now U.S. Pat. No. 6,942,690 entitled "Single-Piece Endoprosthesis With High Expansion Ratios and Atraumatic Ends," which is a continuation-in-part of application Ser. No. 09/837,353 filed Apr. 17, 2001 now abandoned entitled "Single Piece Endoprosthesis with High Expansion Ratios," which is a continuation-in-part of application Ser. No. 09/546,966 filed Apr. 11, 2000 entitled "Single Piece Thick-Walled Endoprosthesis."

BACKGROUND OF THE INVENTION

This invention relates to medical devices for the treatment of vascular diseases generally referred to as endoluminal prostheses. A variety of such devices are available for a broad range of treatment modalities. Examples of such devices are "vascular grafts" and "stents." Vascular grafts are typically used to treat weakened areas of vessels known as aneurysms. Stents are typically used to prop open a narrowed or stenosed vessel.

Stents and grafts may be delivered intraluminally through a narrow incision or a puncture in the patient's skin. The device may be mounted on a delivery catheter and inserted into a corporeal lumen through the skin. The device and catheter are then advanced through the various lumens to the site to be treated. To accomplish this, stents and grafts are generally collapsible for delivery and expansible for treatment.

Vascular grafts are primarily composed of an artificial lumen which isolates the natural lumen from the flow of bodily fluids, such as blood. Grafts may incorporate attachment devices to secure the graft into the natural lumen and keep the graft expanded. Stents are typically formed of metallic wires or bars configured in a cylinder. Prior art stents for sealing a graft to corporeal lumen include narrow, sharp tails that can cause wear to the relatively soft graft. The wear is a function of the radial force of the stent, the sharpness of the stent, and the amount of relative motion between the stent and the graft.

The prior art also teaches methods of manufacturing stents from tubular shape material. Such methods require the manufacturer to remove material from radial surfaces to produce the stent pattern. Raw tubular shape material, as well as processing tubular shape material, is relatively more expensive than the cost and processing of the material in other forms.

Hence, those skilled in the art have recognized a need for providing a prosthesis which produces less wear between the prosthesis and the softer graft material. The need producing stents with non-tubular shape materials has also been recognized. The present invention fulfils these needs and others.

SUMMARY OF THE INVENTION

Briefly and in general terms, the present invention relates to an improved endoluminal prosthesis. This prosthesis may function as a stent or as a means to secure an endoluminal graft in a corporeal lumen such as an artery. The stent may include flattened bulbous tails to reduce the amount of wear between the stent and the softer graft material or corporeal lumen tissue. Stents typically are used to ensure the patency of diseased corporeal lumens by resisting collapse and occlusion. Endoluminal grafts typically are used to isolate diseased corporeal lumens from the flow of bodily fluids. The present invention also relates to a method of producing a tubular stent from a flat sheet of material.

The prosthesis incorporating the present invention is configured as a series of intermittently merging curved beams (e.g. leaf springs) formed into a cylinder. This cylindrical structure is capable of being compressed into a small diameter and expanded into a large diameter. To facilitate both compression and expansion the beams have a cross-section which is greater in the radial direction (thickness) than in the circumferential direction (width). The beams of the present invention are also generally continuously curved to reduce or minimize stress concentrations in the structure. The beams straighten during compression until they are nearly straight.

While compressed the thickness of the beams prevents overlap. In a tightly packed configuration, the curved beams straighten out, come together and generally lie flat in close proximity to each other. The beams resist overlap because the thickness of each beam requires substantial radial displacement to move over or under the adjacent beam. The compression of the prosthesis may be maximized by configuring the beams to fit together tightly in a collapsed condition.

While expanded and during expansion, the thickness of the beams and the configuration of the beams increase the strength of the prosthesis and reduce or minimize stress concentrations. Thicker beams provide for more material in the radial direction to prevent radial collapse. The curved configuration of the beams spreads the bending due to expansion throughout the entire length of the beam. This prevents one area of the beam from generating most of the bending and withstanding resultant stress concentrations.

In various preferred embodiments of the present invention, further improvements distribute stresses throughout the beams more evenly. For example, the extreme ends of adjacent beams may be connected by a loop or eyelet connector. In such an embodiment the stresses from bending due to compression of the prosthesis concentrate in the loop portion of the connector until the lower portion of the connector just adjacent to the loop portion closes on itself, bringing the adjacent beams into contact. Further compression after that point concentrates stresses in the beam below the loop. A similar result can be achieved by configuring the beams to form a significant area of contact adjacent other types of connectors prior to full compression of the prosthesis.

The present invention is a single integrated structure without welds or fasteners. This may be accomplished by removing almond-shaped cells from a thick-walled cylinder. This eliminates the need to construct the prosthesis from individual pieces and possible weak points created by fasteners or joining.

In a first embodiment, the prosthesis may have curved beams which are only merged to adjacent beams at their end points. This creates a single repetitive pattern around the circumference of the cylinder, with each beam merged to opposite adjacent beams at opposite end points. This embodiment may be viewed as the simplest structure to include the invention described herein. It includes alternating half-cells divided by curved beams. This embodiment is not necessarily short, as the beams may be of any length. However, it may be viewed as the shortest configuration for any given cell size.

In a second embodiment, the prosthesis may have curved beams like leaf springs which are repeatedly merged to alternating adjacent beams throughout their length. This second embodiment may also be viewed as the single repetitive pattern of the first embodiment repeated throughout the length of the prosthesis. For example, a prosthesis may be comprised of two or more of the single pattern prosthesis connected end to end. Instead of actually connecting the prosthesis, they may be formed as a single structure. Thereby, the beams could be viewed as continuous throughout the length of the prosthesis. The beams would then have many curved portions which bring them in connection with alternating adjacent beams at merge sections.

The prosthesis may also embody these curved beams forming individual cylindrical elements and connected together by separate elements. Thus, a variety of prosthesis may be formed by connecting different cylindrical elements together with different connecting elements. One configuration includes cylindrical elements having curved beams which are only merged to adjacent beams at their end points connected to cylindrical elements having curved beams which are repeatedly merged to alternating adjacent beams throughout their length. This provides a prosthesis having varying strength and flexibility throughout its length.

In the compressed condition the prosthesis may be intraluminally inserted and delivered within a corporeal lumen. Once delivered to the site to be treated, the prosthesis may be expanded and imbedded into the interior of the lumen. Various methods for intraluminally expanding prostheses are well-known in the art. Expansion due to spring forces is particularly suited for this invention. The superelastic properties of Nickel-Titanium alloys (for example Nitinol) allow a great amount of expansion and compression of structures without permanent deformation. Thus a prosthesis made of such material may be compressed into a very small configuration, and will spring back into a preset form when released. Other known methods of expansion include balloon expansion, and expansion due to the highly elastic properties of certain alloys.

The present invention may also be balloon expandable. To expand the prosthesis by balloon an angioplasty-type dilation catheter is inserted through a compressed or not-fully expanded prosthesis until the balloon portion of the catheter is longitudinally aligned within the prosthesis. The balloon is then expanded forcing the prosthesis radially outwardly.

Once expanded the prosthesis remains in the expanded condition, and the strength of the prosthesis resists radial collapse. When used alone the prosthesis can expand and resist re-collapse of a previously collapsed or stenosed corporeal lumen. When used in combination with a graft, the prosthesis can maintain the graft open and secure the graft to the vessel.

Additional preferred embodiments of the present invention may provide benefits for high-expansion ratios. That is, the prosthesis may be configured to readily withstand high degrees of expansion and compression. Prostheses having loop or eyelet connectors according to this invention may also include beams of different lengths. Alternating pairs of beams having longer lengths and shorter lengths provide a more controlled expansion. This configuration also permits the eyelets of the shorter length beams to nestle below the eyelets of the longer length beams upon compression. A further feature aiding the expansion of the prosthesis includes varying the widths of the individual beams. For example, configuring beams having longer lengths with greater widths will improve the prosthesis ability to accomplish high expansion. Furthermore, varying the width along the length of the beam may also improve the expansion and compression abilities of prosthesis.

Other configurations of the prosthesis may be beneficial when the prosthesis is used in combination with a graft. The ends of prosthesis which are to be configured within a graft may include a flattened bulbous tail. Such an extension of the prosthesis prevents wear on the fabric of the graft. Eyelets on the ends of the prosthesis may also be used for stitching the prosthesis together with the graft. Eyelets provide a good anchoring point for such stitching. Various combinations of connected prosthesis according to the present invention may be used within grafts.

In another aspect, the invention relates to a prosthesis or stent having a plurality of cells. Each cell has a bottom end and a top end. A flattened bulbous tail is at the bottom end of at least more than one of the cells. A flattened bulbous tail may also be at the top end of at least more than one of the cells. Alternatively, the top end of each cell may include an apex having a smaller surface area than the flattened bulbous tail. To facilitate compression of the stent for delivery, adjacent flattened bulbous tails may be staggered longitudinally and the flattened bulbous tails may contour into the body of the stent. The circumference of the bottom and top ends of the stent may also include a rounded or chamferred edge.

In a further aspect, the invention relates to a method of manufacturing a stent from a flat member that includes a first surface and a second surface. Material is removed from the flat member such that the remaining material forms a pattern of a circular array of cells of a desired stent pattern. A mandrel having an outside surface with a shape is placed at the center of the pattern on the first surface of the flat member and the flat member is formed around the mandrel, thereby causing the flat member to assume a seamless tubular shape and becoming a tubular member.

The flat member may include a Nitinol sheet. The removal step may include chemical etching, laser cutting, electrical discharge machining, water-jet cutting, or stamping the stent pattern from the flat member. The outside surface of the mandrel may include a cylindrical shape having a diameter within the range of 20 mm to 34 mm. The forming step may include placing a collar on the second side of the flat member around the center of the pattern. The collar includes an inner surface and an outer surface with the inner surface having the same shape as the mandrel, but being larger than the outside surface of the mandrel. The size difference between the outside surface of the mandrel and the inside surface of the collar is about the same as the thickness of the flat member. The forming step may further include providing relative movement between the mandrel and the collar so that the collar causes the flat member to surround the outside surface of the mandrel, thereby causing the flat member to become the tubular member. The method may further include the step of heat treating the tubular member. The tubular member may be heat treated to a temperature of around 280° C. for a duration of around three minutes, then cooled immediately. The heat treating step may be performed while the tubular stent it is housed between the mandrel and the collar.

These and other advantages of the invention will become more apparent from the following detailed description of the preferred embodiments. When taken in conjunction with the accompanying exemplary drawings, the person of skill in the art will appreciate that various embodiments incorporate the present invention.

BRIEF DESCRIPTION OF THE DRAWINGS

FIG. 13 is a flat pattern view of a portion of a prosthesis including alternative embodiments of variable thickness beams;

FIG. 14 is a flat pattern view of a portion of a prosthesis including additional alternative embodiments of variable thickness beams;

FIG. 22a is a flat pattern view of a prosthesis having a flattened bulbous tail at a bottom end of each of the cells of the prosthesis;

FIG. 22d is a cross-sectional view depicting an end of the prosthesis of FIG. 22a having a radius along an edge;

FIG. 22e is a cross-sectional view depicting an end of the prosthesis of FIG. 22a having a chamfer along an edge;

DETAILED DESCRIPTION OF THE PREFERRED EMBODIMENTS

The following description, as well as the Figures, describe embodiments of the invention. These embodiments are exemplary of the inventors known uses of the invention, and are not intended to limit the scope of the claimed invention. Those skilled in the art of endoluminal devices will appreciate that the invention described herein may encompass many embodiments.

As shown in the Figures, the present invention relates to an endoluminal prosthesis. More particularly, the invention is an expandable and compressible prosthesis for repairing corporeal lumens. The prosthesis may be formed from a metallic cylinder by removal of cells. The invention also discloses a prosthesis with a flattened bulbous tail. The invention further discloses a stent being formed from a flat sheet of material.

Figure 1:
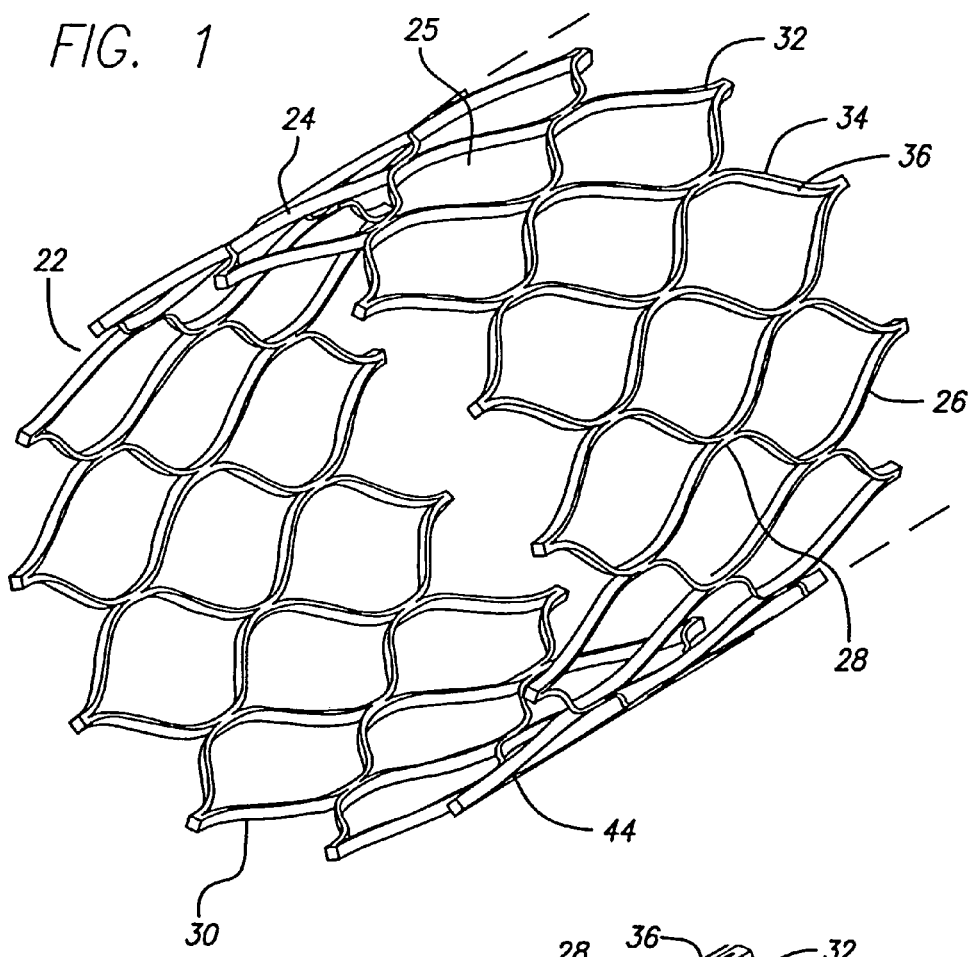
FIG. 1 is a perspective view of a first embodiment of the prosthesis in an expanded condition.
Figure 2:
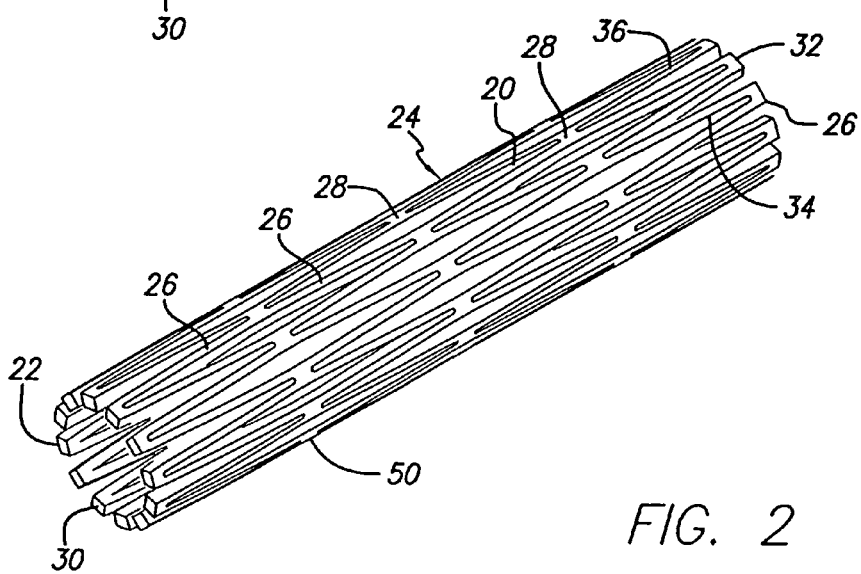
FIG. 2 is a perspective view of the first embodiment of the prosthesis in a compressed condition.

As depicted in FIGS. 1 and 2, the result of removing cells 20 from the metallic cylinder 22 is a prosthesis 24 having a series of curved beams 26 and merge sections 28. It is to be recognized that the prosthesis 24 shown in FIG. 2 can be compressed, where desired, to a smaller diameter such that the cells 20 are essentially defined by slits (not shown).

Figure 5:
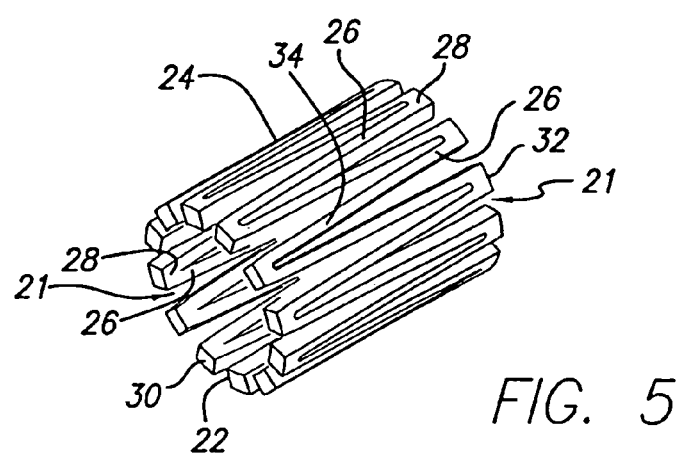
FIG. 5 is a perspective view of a second embodiment of the prosthesis.

The beams 26 are generally longitudinal members circumferentially spaced about the prosthesis 24. In one embodiment, as depicted in FIG. 5, the ends of these beams 26 merge with the ends of circumferentially adjacent beams to form the merge sections 28 only at the ends of the prosthesis. The ends of each beam 26 merge with one adjacent beam on the forward end 30 and the opposite adjacent beam on the rear end 32. This creates a single circumferential pattern of staggered half-cells 21 divided by beams 26. (For comparison, a full cell 25 is identified in FIG. 1). Preferably, the beams 26 each include at least two curved segments 34 of opposite orientations and an inflection point 36 near the mid-point of the beams.

In the embodiment depicted in FIG. 5, the merge sections 28 include either the forward ends 30 or rear ends 32 of two such beams 26 as well as the ends of the prosthesis. These merge sections 28 are also circumferentially spaced about the prosthesis 24, preferably equidistantly.

Figure 6:
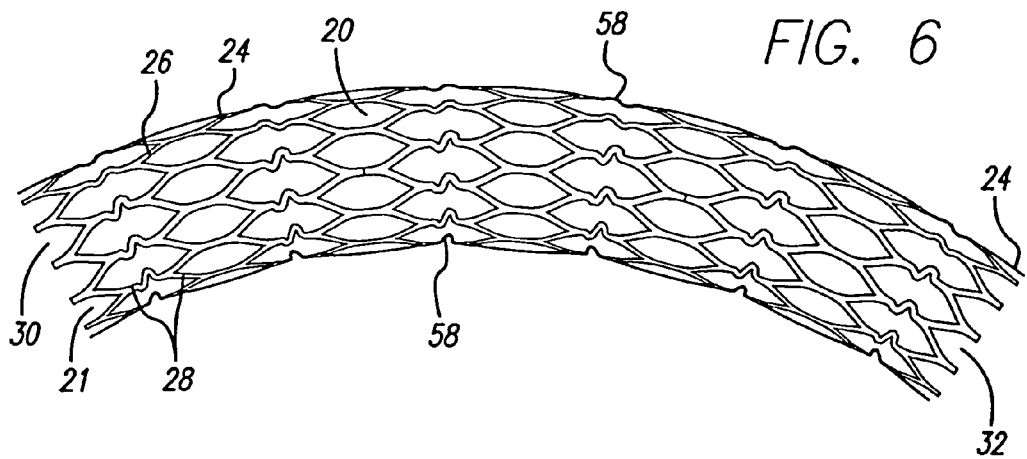
FIG. 6 is a side view of a third embodiment of the prosthesis.

The single pattern as depicted in FIG. 5 may be extended to build longer prostheses 24. This may be done by extending the length of each beam 26 with additional curved segments 34 and forming additional merge sections 28. This forms the prosthesis 24 as depicted in FIGS. 1 and 2. Alternatively, multiple single patterns may be connected with a separate connector element 58. The connector elements 58 may have various configurations and be distributed throughout the prosthesis 24 in a variety of arrangements. Such a prosthesis 24, having "S"-shaped connector elements at each merge section is depicted in FIG. 6. Other embodiments (not shown) may have connectors with other shapes only at every second or third merge section. Such embodiments may have advantages in providing longitudinal flexibility to the prosthesis 24.

In the embodiments depicted in FIGS. 1 and 2 the beams 26 may extend beyond the first merge sections 28 to form additional merge sections 28. This configuration may also be viewed as the merge sections 28 connected end-to-end with opposite facing merge sections 28. This may provide for a prosthesis 24 of greater lengths. The continuous beams 26 of this embodiment merge with adjacent beams 26 repeatedly and alternately throughout their length. The continuous beams are comprised of multiple curved segments 34. The merge sections 28 may also contain flat segments (not shown).

Figure 3:
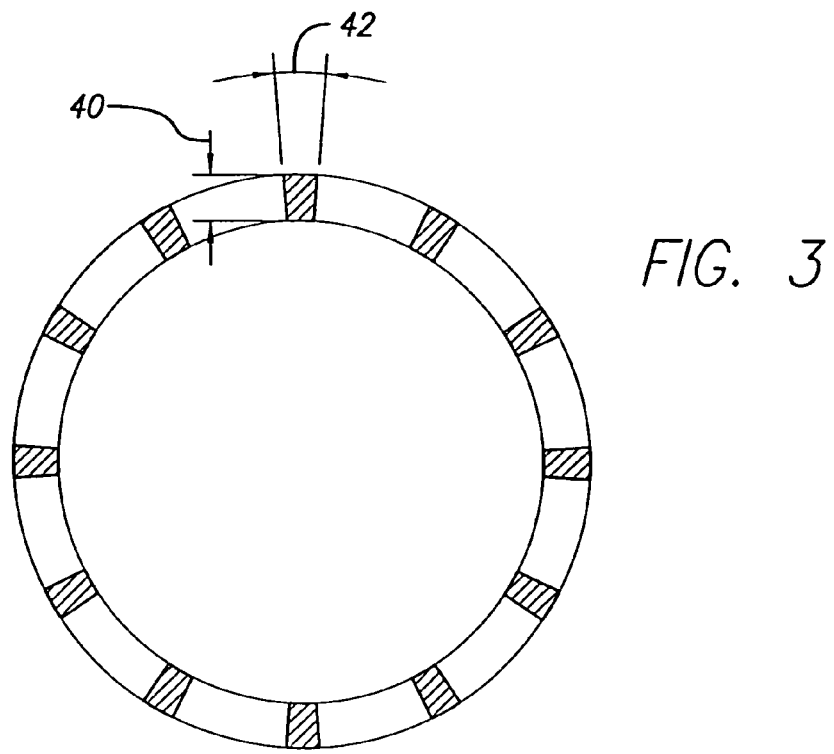
FIG. 3 is a cross-sectional view of the first embodiment of the prosthesis in an expanded condition.
Figure 4:
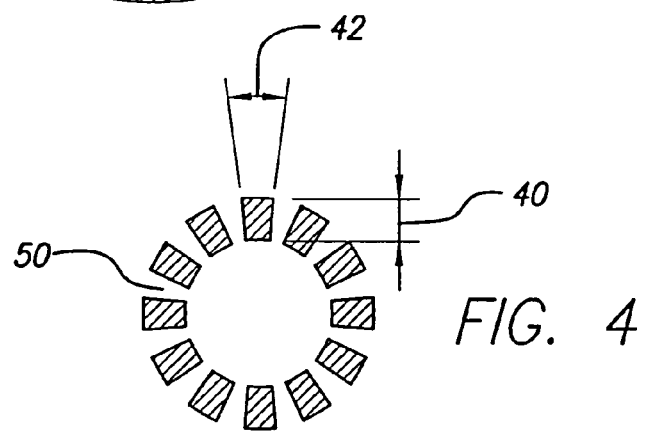
FIG. 4 is a cross-sectional view of the first embodiment of the prosthesis in a compressed condition.

As depicted in FIGS. 3 and 4 the prosthesis 24 is preferably formed from a thick-walled cylinder 22. The difference between the external radius of the cylinder and the internal radius of the cylinder defines a radial thickness 40. Preferably, the cells 20 of the prosthesis 24 are removed such that the remaining beams 26 have a width (measured circumferentially) 42 that is less than the radial thickness 40. A typical design might have dimensions of 0.007" circumferential width 42 and 0.014" radial thickness 40. This defines a deep cross-section for the beams 26. To take advantage of the benefits of this invention, the radial thickness 40 of the beams 26 needs to be substantially greater than the circumferential width 42. Preferably, the radial thickness 40 will be at least one and one-third (1⅓) times the circumferential width 42.

Figure 7:
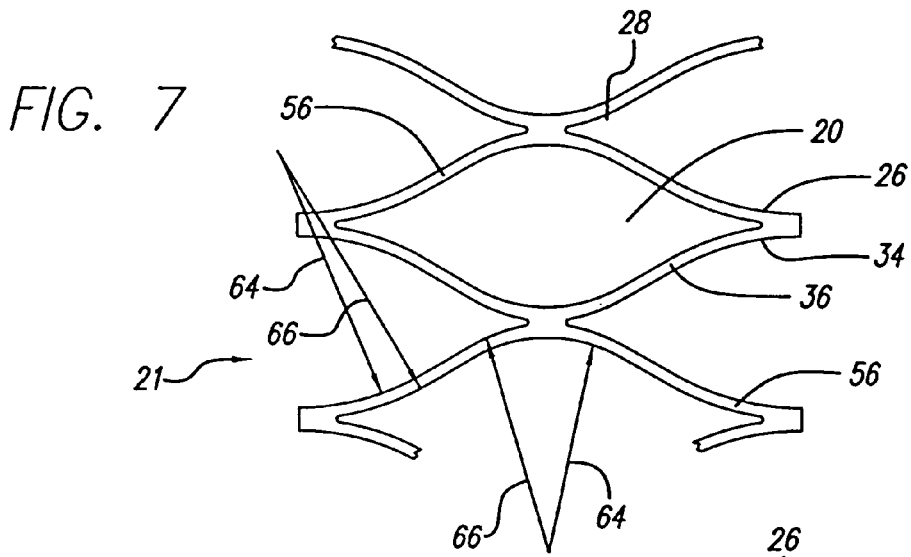
FIG. 7 is a top view of a portion of a flat pattern for the prosthesis.

A theoretical flat pattern of the beams 26 and merge sections 28, as depicted in FIG. 7 reveals the novel configuration of the beams. Preferably, each beam 26 is continuously curved, alternating between curves 56 of opposite orientations throughout its length. In this ideal configuration, the beams 26 form inflection points 36 between the opposite facing curves 56.

Each curve 56 in each beam 26 is defined by two radii, an internal radius 64 and an external radius 66. The difference between these radii define the circumferential width 42 of the beam 26.

The continuously curved configuration of beams 26 disposed longitudinally along a cylinder, provides some of the unique properties of this invention. As the cylinder is expanded from a partially compressed configuration 50, the radii of each curve 56 within each beam 26 becomes smaller as the beams spread apart. Since the beams 26 are ideally continuously curved, the bending is spread throughout the entire length of the beam 26. This spreads the resultant stresses throughout the beam 26 and reduces or minimizes stress concentrations.

As depicted in FIGS. 2 and 4 the use of deep cross-sections has significant advantages for collapsing the prosthesis 24 in preparation of intraluminal delivery. The deep cross-section allows for significant compression without incidental overlapping of the beams 26. The large radial thickness 40 of the beams 26 prevents one beam from extending over the top of another.

As depicted in FIGS. 1 and 3 there are also advantages to the use of deep cross-sections in expansion of the prosthesis 24. In general, as a cylindrical, expandable prosthesis is expanded, longitudinally-oriented members of the collapsed prosthesis tend to bend circumferentially. The relatively narrow width of the beams 26 of the present prosthesis 24 permits circumferential bending without inducing high stress concentrations. The large overall cross-sectional area of the beams 26 prevents re-compression of the prosthesis 24. The configuration of the curved segments 34 spreads the stresses induced by expansion across the entire length of the beams 26, also reducing stress concentrations. In a preferred embodiment, the prosthesis is self-expandable. Alternatively, the prosthesis may be expanded by balloon.

FIGS. 1 and 3 and FIGS. 2 and 4 depict two separate configurations of the prosthesis 24. The prosthesis 24 of the present invention has an expanded configuration 44 while deployed in the lumen as depicted in FIGS. 1 and 3. This configuration has a large inner diameter which allows maximum patency of the lumen 46 to be treated. The prosthesis 24 of the present invention also has a second, partially compressed configuration 50 as depicted in FIGS. 2 and 4. This configuration is beneficial to the intraluminal delivery of the device which is facilitated by a smaller external diameter.

In a typical procedure, the prosthesis 24 will be constrained in the compressed configuration 50 within a catheter. The catheter may then be inserted into a small diameter lumen 46, such as the femoral artery. To prevent damage to such an artery the entire system of catheter and prosthesis 24 must have as small a diameter as possible. Small diameters also facilitate the navigation of the prosthesis 24 and catheter through arduous vasculature. Once inserted into such an artery, the catheter and prosthesis 24 may be advanced through the corporeal lumens, possibly to larger arteries for treatment. The prosthesis 24 may then be released from the catheter. Spring forces within the compressed prosthesis of a self-expanding version will force the prosthesis from the partially compressed configuration 50 into the expanded configuration 44. In a preferred embodiment, the spring forces are great enough to expand the lumen of the diseased vessel as the prosthesis 24 expands. These forces are also great enough to impinge the beams 26 into the tissues of the vessel. This impinging secures the prosthesis 24, and possibly an associated graft 52, into place.

Figure 8:
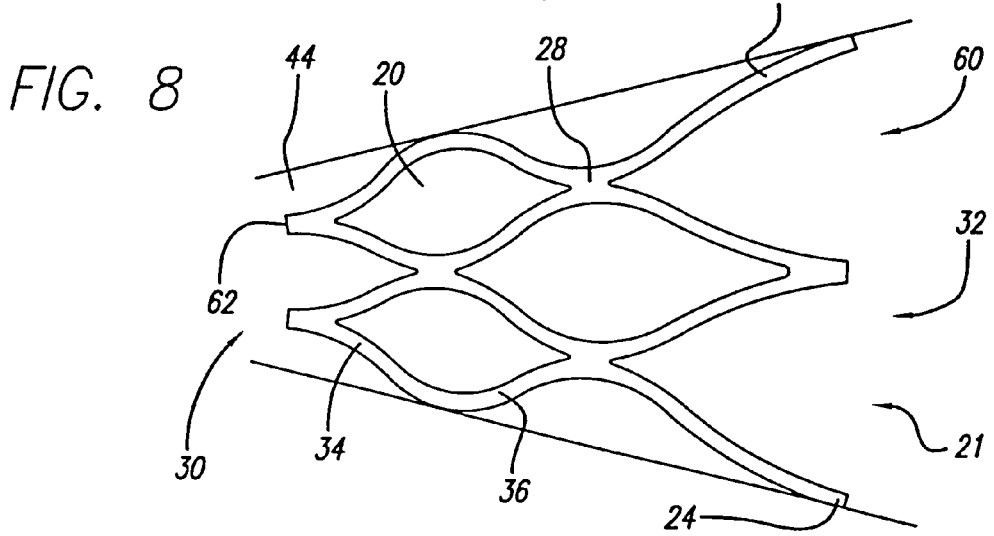
FIG. 8 is a side view of a fourth embodiment of the prosthesis.

Another embodiment of the prosthesis 24, depicted in FIG. 8, has a conical rather than cylindrical shape while in the expanded configuration 44. In this embodiment, the prosthesis 24 has a cylindrical shape in the compressed configuration 50. Upon expansion, however, a broader end 60 of the prosthesis 24 expands more than a narrower end 62. This conical embodiment of the prosthesis 24 is useful in similarly shaped lumens and various configurations of grafts. The broader end 60 may include cells 20 that are longer and wider in the expanded configuration 44 than those at the narrower end 62.

Figure 9:
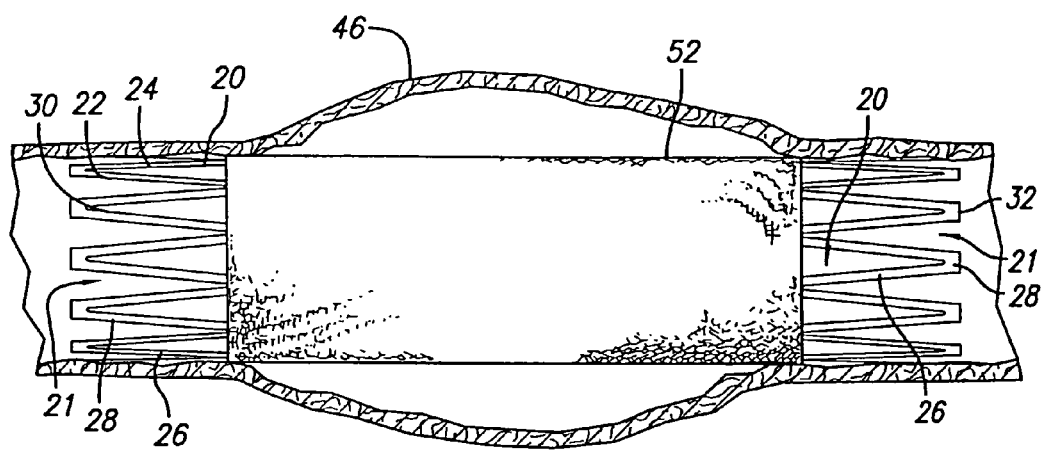
FIG. 9 is a side view of a vascular graft secured in a corporeal lumen by a prosthesis.
Figure 10:
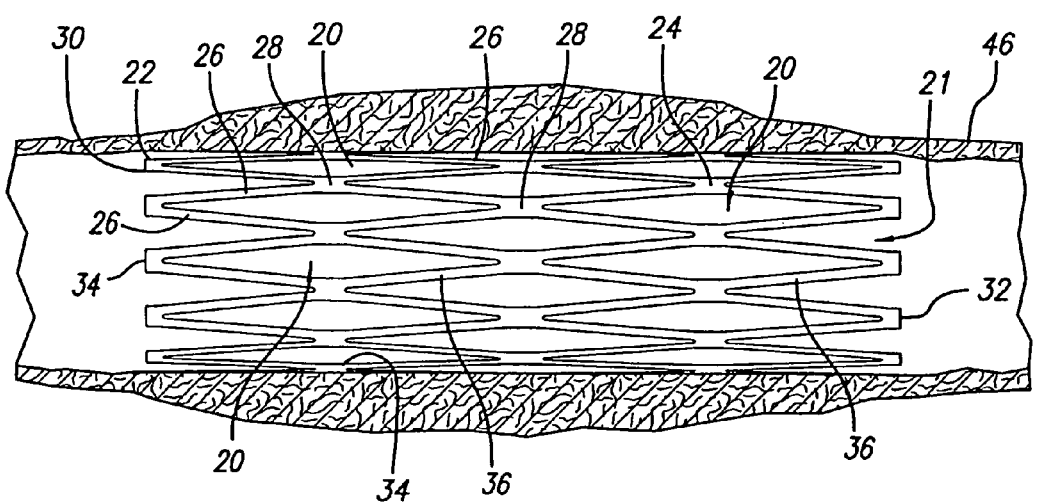
FIG. 10 is a side view of a prosthesis embedded in a corporeal lumen.

The prosthesis 24 of the current invention may be used in a variety of procedures, two of which are depicted in FIGS. 9 and 10. As depicted in FIG. 9, one or more prostheses embodying the present invention may be used in the treatment of aneurysms. An aneurysm is a weakening of the vessel wall of a vein or artery which causes a sack, or possibly a rupture, to form in the lumen 46. When an aneurysm forms in the abdominal aorta, the condition can be life-threatening. A known treatment for aneurysms is the intraluminal delivery and implantation of a vascular graft 52. Such a graft 52 bypasses the sack formed by the aneurysm and isolates the weakened tissues from the blood flow. To operate properly, the graft 52 must have leak-proof fixation to the healthy vascular tissue on either side of the aneurysm. The prosthesis 24 described herein may provide that fixation at one or more ends of the graft 52. The prosthesis 24 may also extend throughout the length of the graft 52. When expanded, the prosthesis 24 may compress the flexible graft material 52 against the arterial wall. Preferably, the prosthesis 24 extends further from the aneurysm than the graft 52 so that parts of the prosthesis 24 are imbedded in healthy tissue. This configuration maintains the patency of the artificial lumen of the graft 52 as well as securing the graft in place by forcing the end of the graft against the wall of the lumen 46. The prosthesis 24 also ensures a leak-proof seal.

As depicted in FIG. 10, a prosthesis 24 embodying the present invention may be used to treat a stenosis or collapse of the lumen 46. Stenosis is often caused by the gradual occlusion of veins or arteries through the build-up of plaque. Preferably a single prosthesis 24 is inserted into the diseased vessel while mounted within a catheter. When the prosthesis 24 is at the location of the narrowing, the prosthesis 24 may be expanded. As depicted in FIG. 10, the spring forces of the prosthesis are preferably sufficient to expand the narrowed vessel. The prosthesis 24 is thereby forced into the tissues of the lumen 46 to secure the prosthesis 24 in place. The structure of the prosthesis 24 resists collapse after expansion.

The prosthesis 24 may be manufactured in the compressed configuration 50, as in FIG. 2, or in the expanded configuration 44, as in FIG. 1, or in any configuration in between. The manufacturing procedure requires the removal of cells 20 from a thick-walled cylinder 22. This may be accomplished with several known manufacturing methods, such as laser cutting, chemical etching, photo-etching, electrical discharge machining (EDM) and mechanical means. Two materials found to be particularly suited to this application are implantable stainless steel and Nickel-Titanium alloys, such as Nitinol.

Figure 11:
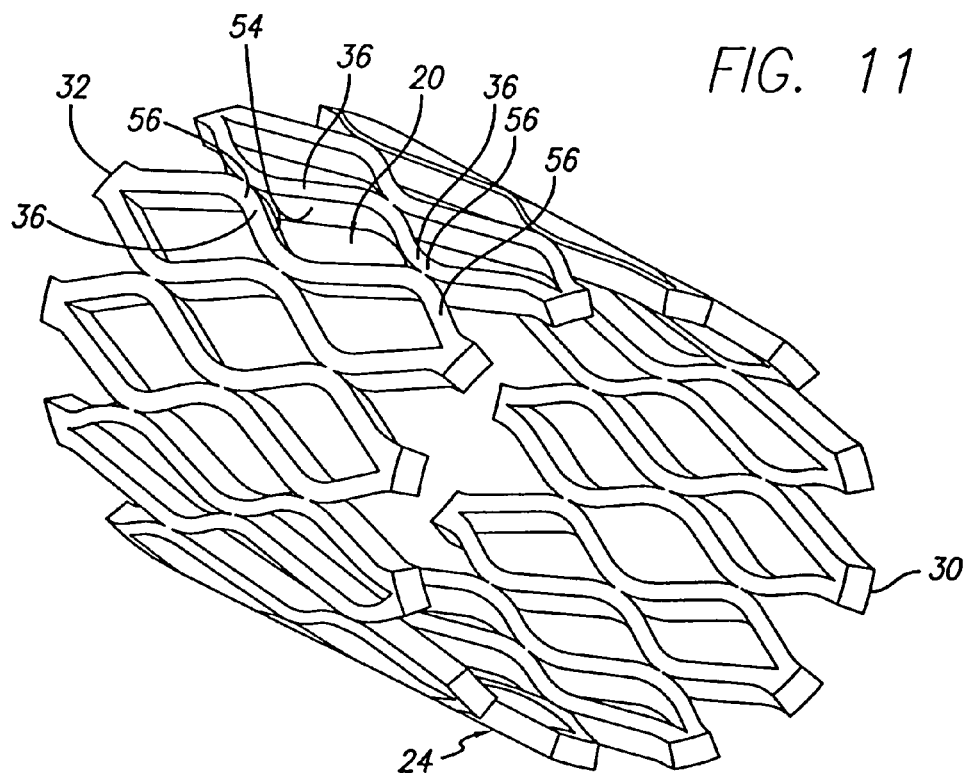
FIG. 11 is a perspective view of a thick-walled cylindrical tube with cells designed therein.

As depicted in FIG. 11, each cell 20 of the endoprosthesis 24 may consist of two sides 54 having three curves 56 and two inflection points 36. Such a configuration produces almond-shaped cells. There may also be flat portions (not shown) designed into the cell 20. These cells 20 are designed on the thick walled cylinder 22 in a pattern which repeats along the length of the cylinder 22. This pattern is repeated with a longitudinal stagger of half a cell 20 around the circumference of the cylinder 22. The pattern also includes half cells at each end of the tube. Upon removal of the cells 20, the remaining material constitutes the prosthesis 24 described herein.

The prosthesis 24 may be formed from a thick walled cylinder 22 approximately the size of the compressed configuration 50. This thick walled cylinder 22 may be a Nickel Titanium alloy. Cells 20 are laser cut into the thick walled cylinder 22 while the thick walled cylinder 22 is mounted over a wire. The cells 20 are formed in a long, narrow configuration with each of the curves 56 having large radii.

After the cells 20 are cut into the thick walled cylinder 22, the prosthesis 24 is cleaned and deburred to eliminate manufacturing irregularities. This may include blasting techniques, acid etching, ultrasonic cleaning and/or other well known methods of cleaning.

The prosthesis may then be stretched into more expanded configurations. One method of expanding the prosthesis is by mechanically stretching it over a mandrel. The mandrel may be specifically designed with pins to maintain the desired curvature of the beams. Once stretched, the prosthesis is annealed to set the new expanded shape of the prosthesis. Annealing can be accomplished by heating the prosthesis within a variety of media, such as air, molten salt, inert gas or vacuum. Annealing at 260-288° C. is appropriate for Nickel-Titanium alloys. After stretching, the prosthesis 24 is cleaned again. This process of stretching, annealing and cleaning can be repeated until the desired configuration is obtained. Once the desired configuration has been obtained, the prosthesis is electropolished by any of the well-known methods.

Alternatively, a prosthesis 24 may be formed from a Nickel Titanium thick walled cylinder 22 approximately the size of the expanded configuration. In this process, cells 20 are cut into the thick walled cylinder in a shorter and wider configuration. This method would eliminate the need to stretch and anneal the prosthesis 24 to achieve the expanded configuration 94.

Figure 12:
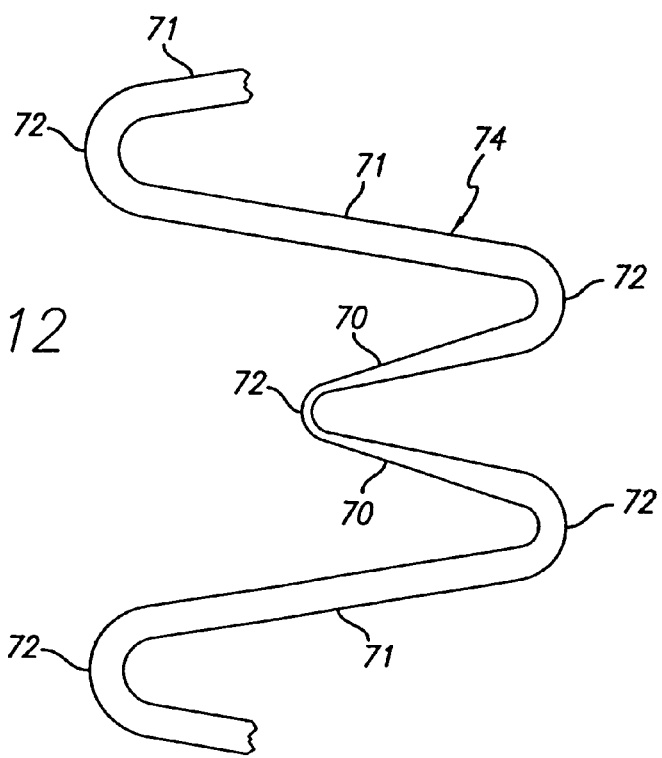
FIG. 12 is a flat pattern view of a portion of a prosthesis embodying variable thickness beams.

As best seen in FIGS. 12-14, it is also contemplated that the beams of a prosthesis may embody variable width beams or struts 70 and generally uniform width beams or struts 71. The incorporation of variable width struts 70 into a prosthesis facilitates uniform expansion. For example, to achieve uniform expansion, it is desirable to have struts 70 of the same width meeting at connecting junctions 72. Asymmetric prosthesis portions 74, 76, as shown in FIGS. 12 and 13, may further require the strut 70 to embody a width that gradually varies along the length of the strut 70. Moreover, as shown in FIG. 14, where a prosthesis portion 78 embodies a plurality of adjacent oriented cells 80, the point of connection 82, 83 between adjacent cells 80 may be varied in length, for example to accommodate a hole 84. To facilitate uniform expansion of such a prosthesis portion 78, the struts 70 extending from a relatively shorter point of connection 82 between adjacent cells 80 can embody a tapering thickness.

Figure 15:
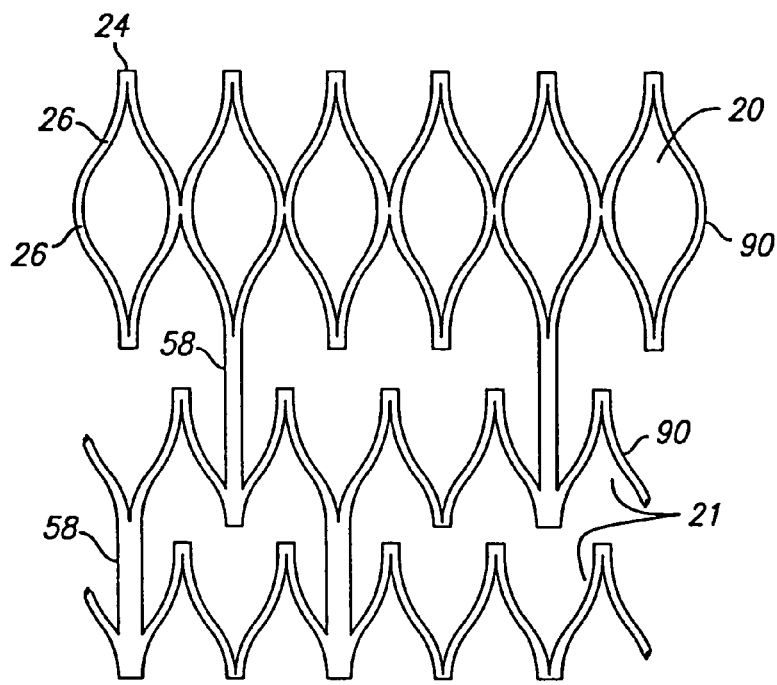
FIG. 15 is a flat pattern view of a portion of a prosthesis including additional alternative embodiments having varying flexibility.

The novel features of the present invention may be applied to configure a prosthesis having variable properties throughout the length of the prosthesis. As an example, and as depicted in FIG. 15, the flexibility of the prosthesis 24 may vary along the length of the prosthesis. To accomplish this, connector elements 58 may be used to combine segments 90 of the prosthesis 24. Each segment 90 may be composed of curved beams 26 in the various configurations described above. In a preferred embodiment, a segment 90 composed of full cells 20 may be combined with multiple segments 90 composed of half-cells 21. The portion of the prosthesis 24 composed of half-cell 21 segments 90 will tend to be significantly more flexible longitudinally and slightly more flexible radially. The invention includes any combination of full cells and half-cells in a prosthesis including, but not limited to, full cells between half-cells.

One application of a prosthesis 24 having variable flexibility throughout its length is for the support of a vascular graft 52. In such an application, the more flexible segments 90 of the prosthesis 24 may be configured to support the artificial lumen 46 of the graft 52. The less flexible segments 90 of the prosthesis 24 may be configured to extend beyond the artificial lumen 46 and into the patients natural lumen. In this manner, the less flexible segments 90 help secure the graft 52 into place, while the more flexible segments 90 support the material of the graft 52.

Figure 16A:
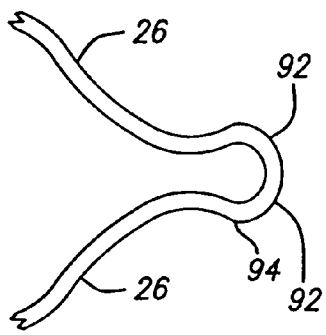
FIGS. 16a and 16b are side views of a first alternative embodiment of the beam ends and connector.
Figure 16B:
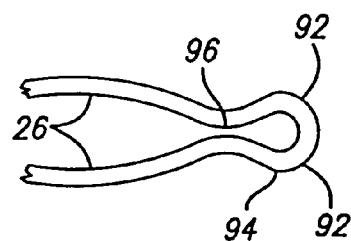

The invention described herein may also embody features to facilitate the high ratios of expansion possible with the prosthesis 24. As depicted in FIGS. 16a and 16b, as well as in FIGS. 17a and 17b, the ends 92 of the beams 26 may be connected in a manner which evenly distributes the stresses incurred by expansion and compression.

An eyelet or loop connector 94 (shown in FIGS. 16a and 16b) may connect the ends of the beams 26. These eyelet connectors 94 distribute the stresses created by compression of the prosthesis 94. As the prosthesis 24 is initially compressed and adjacent beams 26 are brought together, the bending and resultant stresses are initially concentrated in the eyelet or loop portion of the connector 94. Eventually, a contact area 96 is formed at the edge of the eyelet connector 24. As the prosthesis 24 is further compressed and adjacent beams 26 are brought even closer together, the bending and resulting stresses are concentrated at the ends of the beams 26 near the contact area 96. Even further compression may relieve the stresses in the eyelet connector 24 by creating a fulcrum at the contact area 96.

Figure 18:
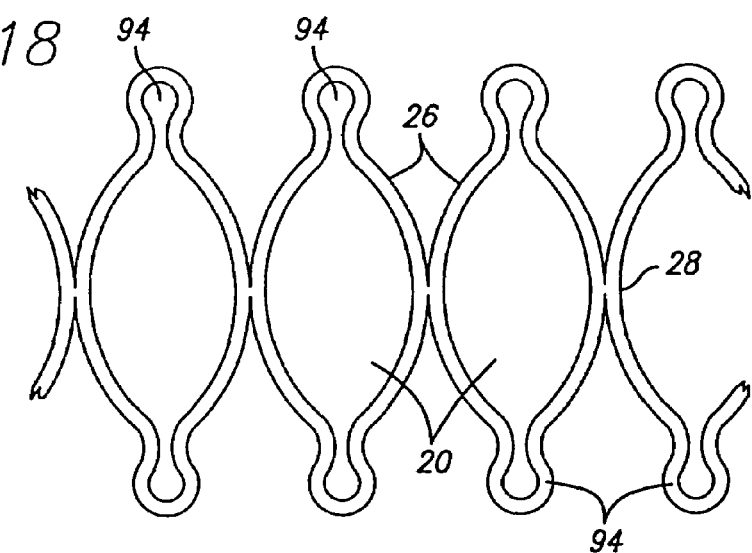
FIG. 18 is a flat pattern view of a first embodiment of a prosthesis having the alternative beam end connectors shown in FIGS. 16a and 16b.

A prosthesis 24 composed entirely of eyelet connectors 94, as depicted in FIG. 18, may facilitate the distribution of stresses induced by high expansion ratios. Thus, the prosthesis 24 of the present invention may be used in particularly large corporeal lumens, such as the abdominal aorta. This same prosthesis 24 may also be introduced into relatively small corporeal lumens, such as the femoral artery. Such an application requires the prosthesis to transition between a highly compressed state for insertion into the femoral artery, to a highly expanded state for implantation into the abdominal aorta. This application, as well as others, induce high stresses on the prosthesis 24 through bending of the beams 26 in expansion and compression.

Figure 17A:
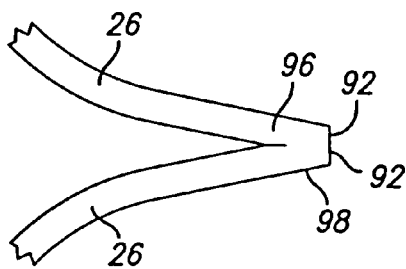
FIGS. 17a and 17b are side views of a second alternative embodiment of the beam ends and connector.
Figure 17B:
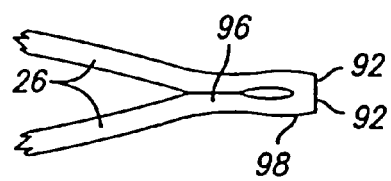

A similar distribution of the stresses may be accomplished by configuring the ends 92 of the beams 26 into increased contact end connectors 98 (FIGS. 17a and 17b). In such a configuration (depicted in FIGS. 17a and 17b), the ends 92 of the beam 26 connect together with a substantial area of contact 96 near the actual connection. As the prosthesis 24 is compressed and the beams 26 are brought closer together, the stresses due to bending are concentrated in the beams 26 near the contact area 96. The contact area 96 expands as the beams 26 are brought closer together and the stress concentrations are thereby distributed along the length of the beams 26.

Figure 19:
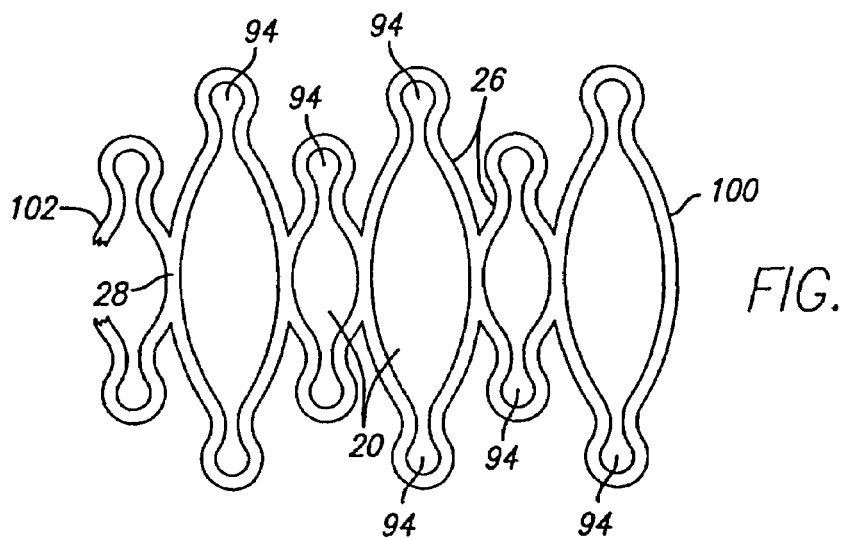
FIG. 19 is a flat pattern view of a second embodiment of a prosthesis having the alternative beam end connectors shown in FIGS. 16a and 16b.
Figure 20:
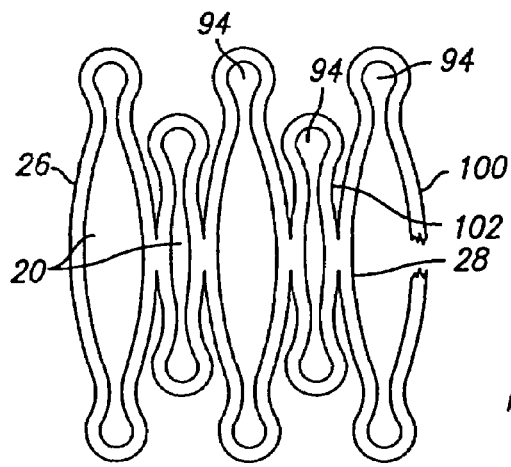
FIG. 20 is a flat pattern view of the prosthesis of FIG. 19 in a collapsed state.

To further support high expansion ratios, the prosthesis 24 of the present invention may be configured to pack tightly for compression into a collapsed state. One example, as depicted in FIGS. 19 and 20 may utilize eyelet connectors 94 aligned to differing heights. That is, every other eyelet connector 94 may be configured upon beams 26 of a first, greater length 100, while each other eyelet connector 94 may be configured upon beams 26 of a second, lesser length 102. Thus the eyelet connectors 94 configured upon beams at the second length would have their greatest width at the same location that the eyelet connectors 94 configured upon beams at the first length have their least width. In this manner, the beams 26 and eyelet connectors 94 fit together in the most compact condition while compressed. Similar results may be accomplished by varying the thickness of the beams 26 and connectors 94.

Varying the circumferential width 42 of the beams 26 may also provide benefits in high expansion ratios. For example, using larger widths on beams 26 of a first, greater length 100 may help control the expansion of the prosthesis 24 and reduce stress concentrations. Varying the circumferential width 42 along the length of individual beams 26 may provide superior nesting when the prosthesis is provided with eyelet connectors 94.

Figure 21:
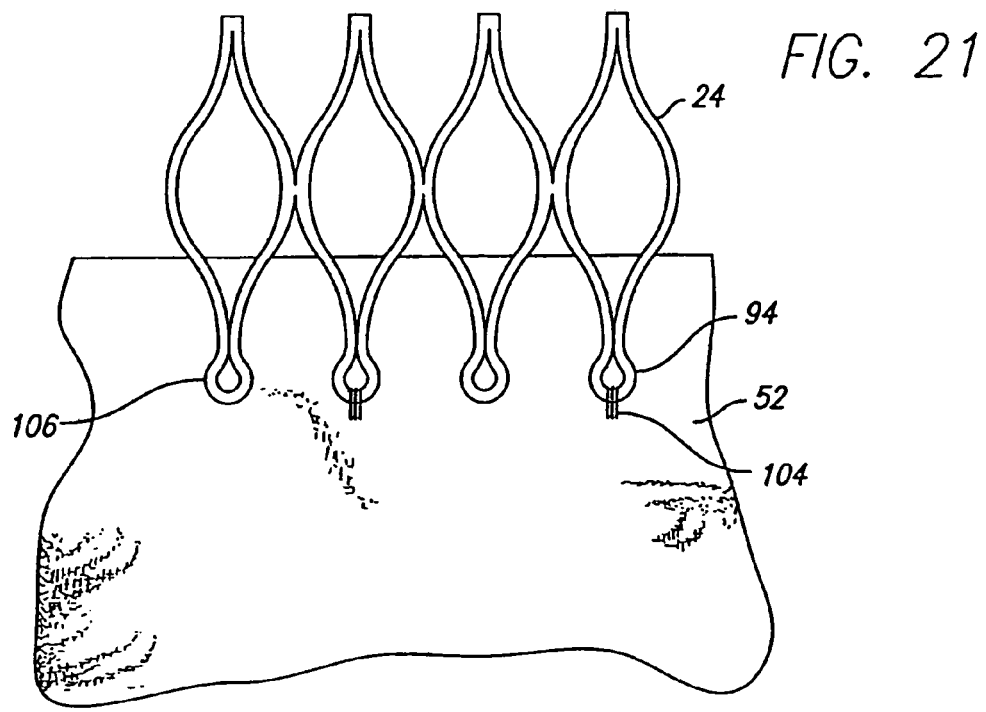
FIG. 21 is a flat pattern view of a prosthesis from within a vascular graft.

Further configurations, as depicted in FIG. 21, may be advantageous when the prosthesis 24 is configured for use in a vascular graft 52. Eyelet connectors 94 may be used to provide an anchor for the stitching 104 between the graft 52 and the prosthesis 24. The merge sections 28 at the end of the prosthesis may include a flattened bulbous tail 106. The tails 106 reduce the wearing on the fabric of the graft 52. Tails 106 may also help control the expansion of the prosthesis 24. Instead of springing open when the ends of the prosthesis 24 are released, the tails 106 may remain constrained within a delivery catheter and provide the prosthesis 24 with a slower, more controlled expansion.

As depicted in FIG. 22a, an alternative configuration of a prosthesis or stent 120 for use in a vascular graft assembly includes a flattened bulbous tail 122 at a bottom 124 end of at least more than one cell 126 of the stent. In one embodiment, the bottom 124 end of each cell 126 includes a flattened bulbous tail 122. Adjacent tails 122 are staggered longitudinally, thus allowing each tail to attain a maximum size without interfering with compression of the stent 120 for packing of the stent into a delivery catheter. The flattened bulbous tails 122 include larger surface areas than the apices 128 at the top 130 of the stent 120.

While a vascular graft assembly typically includes at least one fixation stent that attaches a tubular graft to a corporeal lumen, the flattened bulbous tail stent 120 of the present invention aids in sealing the graft to the corporeal lumen. In one embodiment, the tubular graft of the vascular graft assembly includes a first end region and a second end region. The stent 120 may be located within the first end region of the graft with the flattened bulbous tails 122 of the bottom 124 end of the stent positioned inside the tubular graft and the apices 128 at the top 130 end of the stent located beyond the first end region of the graft. Such placement of the stent 120 positions the apices 128 of the stent external to the graft.

Anytime a stent or prosthesis is deployed in a graft, there is an opportunity for wear. The flattened bulbous tail 122 of the stent 120 reduces the amount of wear between the stent and the softer material of the vascular grafts. Prosthesis or stent to graft wear is a function of the radial force per unit area of the stent, the sharpness of the stent, and the amount of relative motion between the stent and the graft. In the present invention, the relatively large surface area of the flattened bulbous tail 122 displaces the radial force of the tail over a larger area, thereby effectively reducing the radial force per unit area of the stent, and the sharpness of the stent 120 is decreased by the circular shape of the flattened bulbous tail. By reducing the radial force per unit area and decreasing the sharpness through the use of the flattened bulbous tail, the amount of graft wear for a given stent over a given time is reduced, thereby prolonging the useful life of the graft. The flattened bulbous tail 122 configuration disclosed herein may also be applied to the previously disclosed prostheses and stents.

Figure 22B:
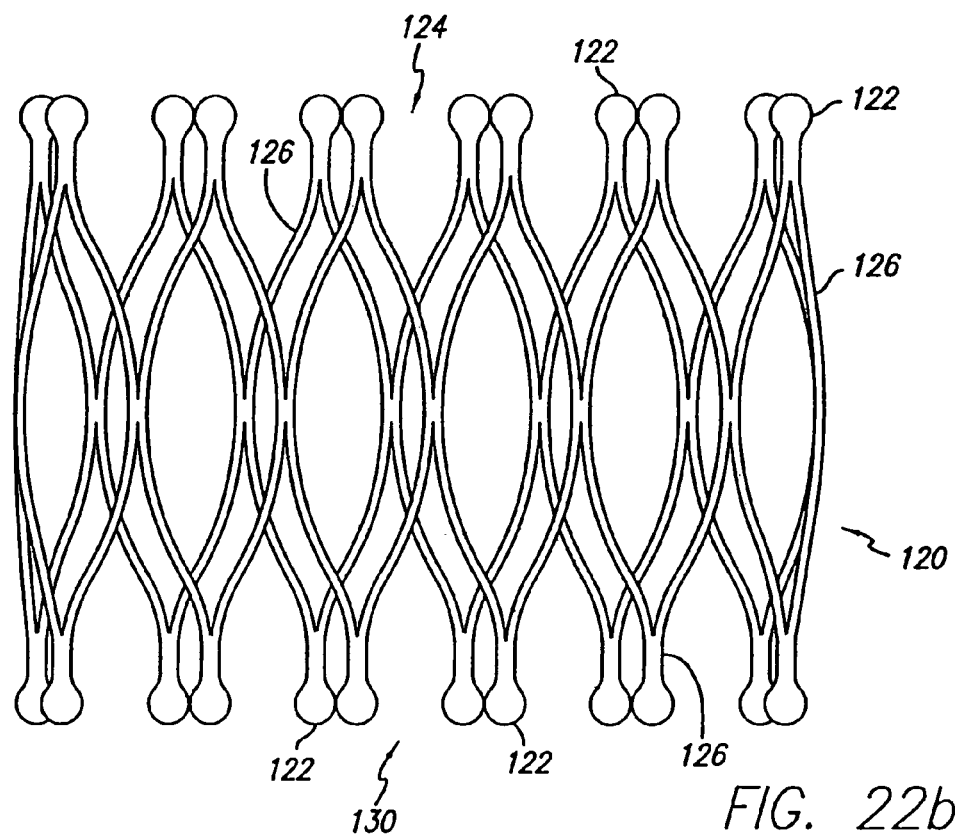
FIG. 22b is a flat pattern view of a prosthesis having a flattened bulbous tail at the bottom end and the top end of each of the cells.
Figure 22C:
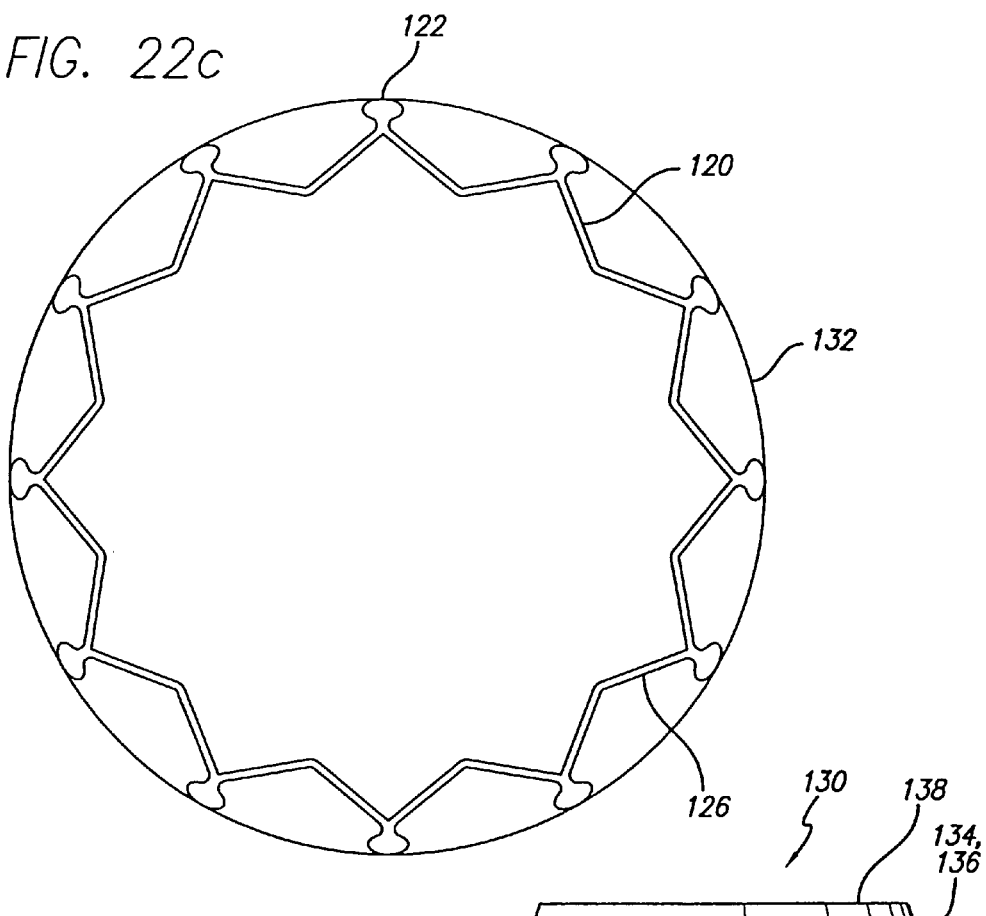
FIG. 22c is a cross-sectional view depicting contact points between the flattened bulbous tails of a prosthesis and a corporeal lumen wall.

Referring to FIG. 22b, flattened bulbous tails 122 may replace the apices at the top 130 end of at least more than one cell 126 of the stent 120 or prosthesis in order to minimize wear at the contact point between a stent and a corporeal lumen wall 132 (FIG. 22c). In one embodiment, the top 130 end of each of the cells 126 and the bottom 124 end of each of the cells within the stent 120 includes a flattened bulbous tail 122. FIG. 22c depicts the contact points between one embodiment of a stent 120 having flattened bulbous tails 122 and the corporeal lumen wall 132. FIG. 22b depicts the flattened bulbous tails 122 at the bottom 124 end and top 130 end of the cells 126 offset longitudinally such that only one half to the flattened bulbous tails occupy the same axial location when the stent 120 is compressed for delivery.

Figure 22F:
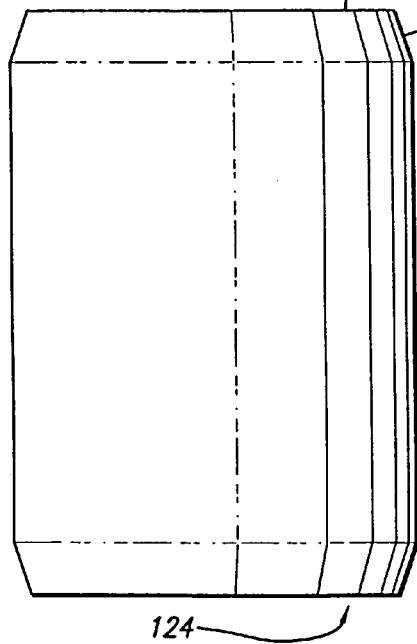
FIG. 22f is a plan view depicting a tubular structure having atraumatic ends.
Figure 23A:
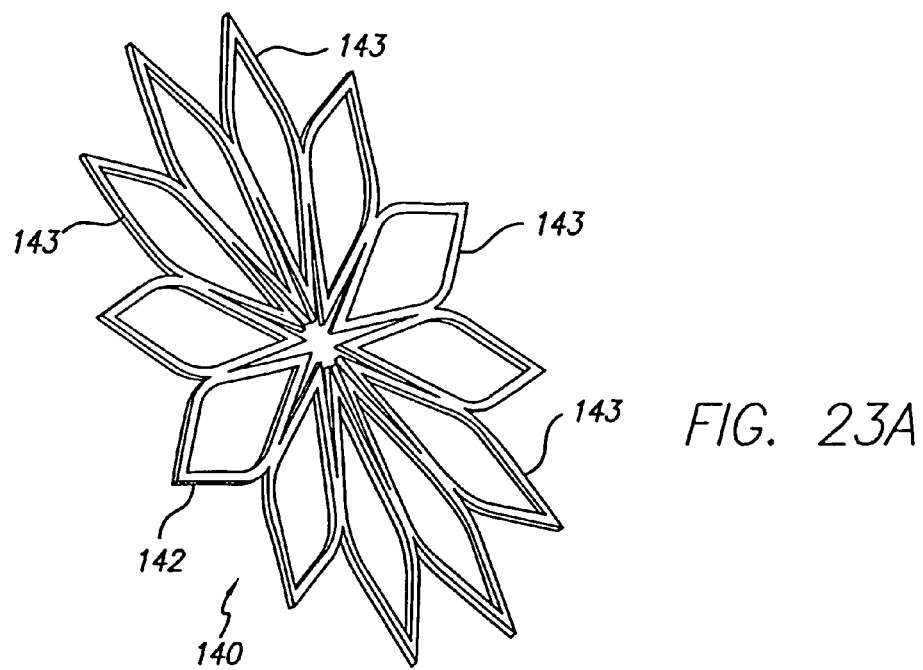
FIG. 23a is a perspective view of a flat pattern layout for a stent design.
Figure 23B:
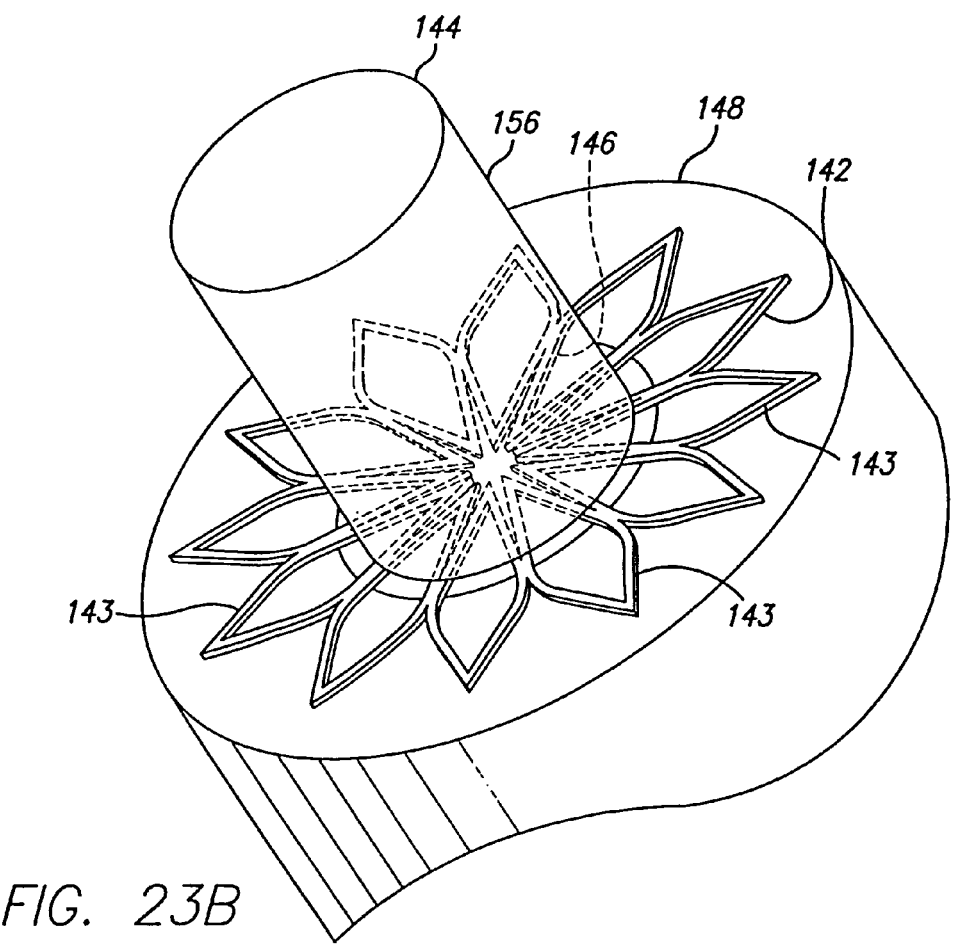
FIG. 23b is a perspective view of the flat pattern layout of the stent of FIG. 23a positioned with a mandrel and a collar prior to forming of the stent into a tubular shape.
Figure 23C:
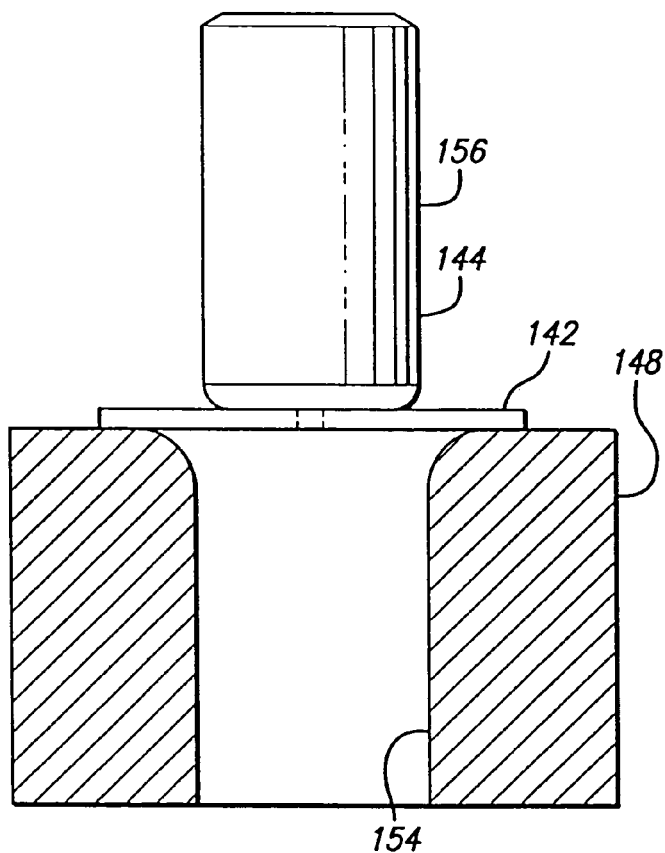
FIG. 23c is an elevation view of the flat pattern layout of the stent of FIG. 23a positioned with the mandrel and collar of FIG. 23b prior to forming of the stent into a tubular shape.
Figure 23D:
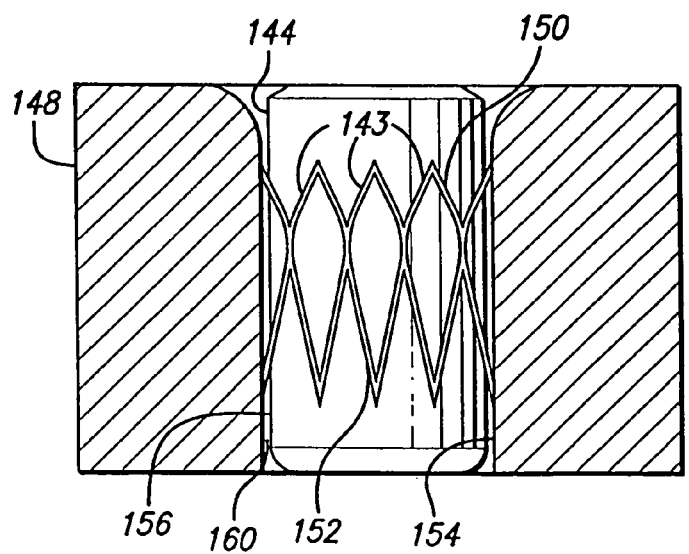
FIG. 23d is an elevation view of the stent of FIG. 23a formed into the tubular shape and positioned between an interior surface of the collar and an exterior surface of the mandrel.

An alternate method of minimizing wear at the contact point between a stent 120 and the corporeal lumen wall 132 or graft material is to grind a radius 134 (FIG. 22d) or chamfer 136 (FIG. 22e) around the circumference of the bottom 124 end and the top 130 end of each of the cells 126. Alternatively, if the stent 120 is laser cut from a Nitinol tube 138 (FIG. 22f), the bottom 124 end and top 130 end of the tube may be ground prior to cutting the cell 126 pattern within the stent. With a radius 134 ground around the circumference of the bottom 124 or top 130 end of each of the cells 126, the contact point between the stent 120 and the vessel lumen wall 132 or graft material is the tangent point of the radius.

A method for fabricating stents from a flat sheet of material is depicted in FIGS. 23a-23d. The general geometry of the stent pattern 140 (FIG. 23a) can be cut directly from a workpiece 142 of a substantially flat piece of material. In a preferred embodiment, the workpiece 142 includes a shape memory sheet metal material, such as a Nitinol sheet. Cutting the general geometry of the stent pattern may be accomplished by any of several known manufacturing methods, such as laser cutting, chemical etching, photo-etching, electric-discharge machining (EDM), water-jet cutting, stamping, and other mechanical means.

Material removal, such as the cutting of the stent pattern 140, is easier to perform on a flat piece of material than on a tubular piece of material. For instance, when cutting a stent pattern from a tubular piece of material, it is often necessary to place a secondary filler material into the lumen of the tube to prevent damage to one side of the tube while an opposite side of the tube is being cut. Also, it is often necessary to rotate a tubular piece of material about its axis while a stent pattern is being cut into it. While these steps may add to the complexity of cutting a stent pattern into a piece of material, they may also add to the cost to cut the stent pattern. Further, the cost of raw tubular material is often higher than the cost of sheet material. Therefore, producing a tubular stent from a flat sheet of material may reduce the cost of producing the stent.

The stent pattern 140 may include a circular array of cells 143. After the stent pattern 140 is produced, a cylindrical mandrel 144 may be placed at the center 146 of the pattern 140 within the workpiece 142 from a first side of the flat sheet and a collar 148 may be placed around the center of the pattern on a second side of the flat sheet. Relative movement of the collar 148 and the mandrel 144 toward each other causes the flat workpiece 142 to form around the mandrel and to assume a seamless tubular shape 150 (FIG. 23*d*) between the mandrel and the collar. Although a cylindrical-shape mandrel 144 and collar 148 are disclosed, other shapes may also be used, such as a conical shape.

In a preferred embodiment, the outer diameter of the mandrel 144 ranges from 20 mm to 34 mm, depending on the size of the stent 152 to be produced, however a smaller or larger diameter can be used. The mandrel 144 can also incorporate grooves (not shown) or pins (not shown) which coincide with the cells 143 to control or change the shape of the stent 152. The inside surface 154 of the collar 148 may have the same shape as the outside surface 156 of the mandrel 144, but with the collar in place over the mandrel there is a gap 160 all around about the same size as the thickness of the stent 152.

The stent 152 may be heat treated, such as in a furnace (not shown) or in a salt pot (not shown), while housed between the mandrel 144 and the collar 148. During the heat treatment process, the material may be heated to a temperature of around 280° C. (535° F.) for a duration of about three minutes, and then cooled rapidly to set the shape into the material. The method disclosed herein for fabricating stents from a flat sheet of material may also be applied to the previously disclosed prostheses and stents.

While the present invention has been described herein in terms of a prosthesis or stent for the repair of blood vessels, those of skill in the art will readily recognize that prostheses embodying the described invention can be used to treat a variety of corporeal lumens, for example the bronchial tree or intestines. The invention described herein is intended to be limited only by the claims that follow and not by any particular embodiment.

What is claimed is:

1. A vascular graft assembly, comprising:
   a tubular graft having a first end region and a second end region;
   at least one prosthesis having,
   a plurality of cells defined by struts having a first width, each cell having a bottom end and a top end,
   a flattened bulbous tail at the bottom end of at least more than one of the cells, and
   a flattened bulbous tail at the top end of at least more than one of the cells; and
   the at least one prosthesis being located at the first end region of the graft with the bottom end of each cell of the prosthesis positioned inside the tubular graft and the top end of each cell of the prosthesis positioned beyond the first end region and external the tubular graft, wherein each of the flattened bulbous tails has a perimeter and a continuous lateral surface bounded by the perimeter, the continuous lateral surface defining a second width greater than the first width.

2. The vascular graft of claim 1, wherein the bottom end of each cell of the at least one prosthesis includes a flattened bulbous tail.

3. The vascular graft of claim 1, wherein the top end of each cell of the at least one prosthesis includes a flattened bulbous tail.

4. The vascular graft of claim 1, the flattened bulbous tails of the at least one prosthesis contouring into the body of the prosthesis.

5. The vascular graft of claim 1, wherein adjacent flattened bulbous tails of the at least one prosthesis are staggered longitudinally.

6. The vascular graft of claim 1, the at least one prosthesis further comprising:
   a substantially rounded edge about the circumference of the at least one prosthesis at the bottom end; and
   a substantially rounded edge about the circumference of the at least one prosthesis at the top end.

7. The vascular graft of claim 1, the at least one prosthesis further comprising:
   a substantially chamferred edge about the circumference of the at least one prosthesis at the bottom end; and
   a substantially chamferred edge about the circumference of the at least one prosthesis at the top end.

\* \* \* \* \*